United States Patent [19]

Patrick, Jr. et al.

[11] 4,019,500
[45] Apr. 26, 1977

[54] SPONGE RETAINING CUP FOR MEDICAL ELECTRODE

[75] Inventors: Charles T. Patrick, Jr., Centerville, Ohio; David W. King, Connersville, Ind.

[73] Assignee: NDM Corporation, Dayton, Ohio

[22] Filed: May 27, 1975

[21] Appl. No.: 580,622

[52] U.S. Cl. .......................... 128/2.1 E; 128/417; 128/DIG. 4

[51] Int. Cl.² .............................................. A61B 5/04

[58] Field of Search .......... 128/2.06 E, 2.1 E, 404, 128/410, 411, 417, 418, 172.1, DIG. 4; 401/196, 202; 118/270

[56] References Cited

UNITED STATES PATENTS

| | | | |
|---|---|---|---|
| 1,021,522 | 3/1912 | Hinsdale | 401/202 |
| 1,583,087 | 5/1926 | Morse | 128/417 |
| 1,711,375 | 4/1929 | Clark | 401/202 |
| 2,299,296 | 10/1942 | Battle | 401/196 |
| 3,279,468 | 10/1966 | Le Vine | 128/410 |
| 3,701,346 | 10/1972 | Patrick, Jr. | 128/2.06 E |
| 3,882,853 | 5/1975 | Gofman et al. | 128/2.06 E |

*Primary Examiner*—Dalton L. Truluck
*Assistant Examiner*—Lee S. Cohen
*Attorney, Agent, or Firm*—Dybvig & Dybvig

[57] ABSTRACT

A cup for use in medical electrode structures comprises a one-piece body of plastic having a cup shape and thus having a base and a rim. The rim is rounded for comfortable skin contact and has integrally formed barbs projecting inwardly and downwardly toward the center of the cup. The barbs permit a prefilled electrolyte sponge to be dropped into the cup without appreciable resistance from the barbs, but resist any tendency for the prefilled sponge to separate from the cup. Accordingly the cup supports the prefilled electrolyte sponge for contact to the skin of a patient but resists any tendency of the sponge to escape the cup by clinging to the patient's skin.

3 Claims, 4 Drawing Figures

U.S. Patent    April 26, 1977    4,019,500
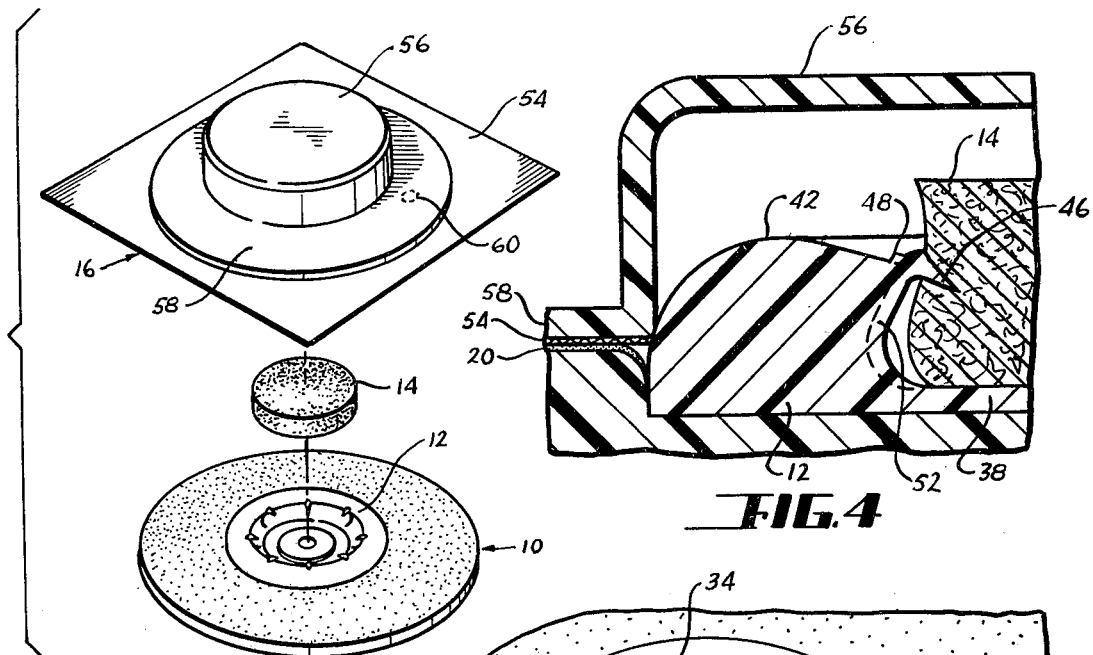
FIG.1
FIG.4
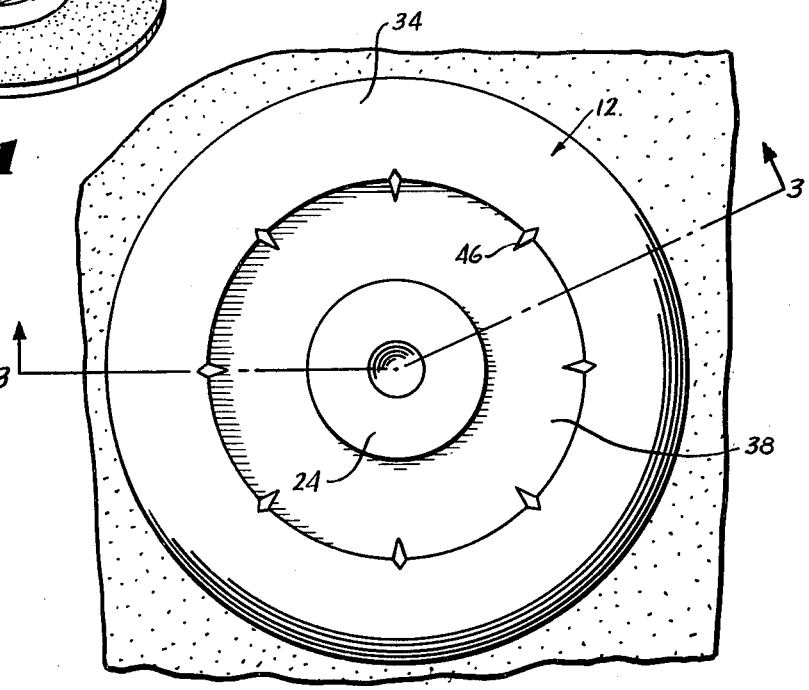
FIG.2
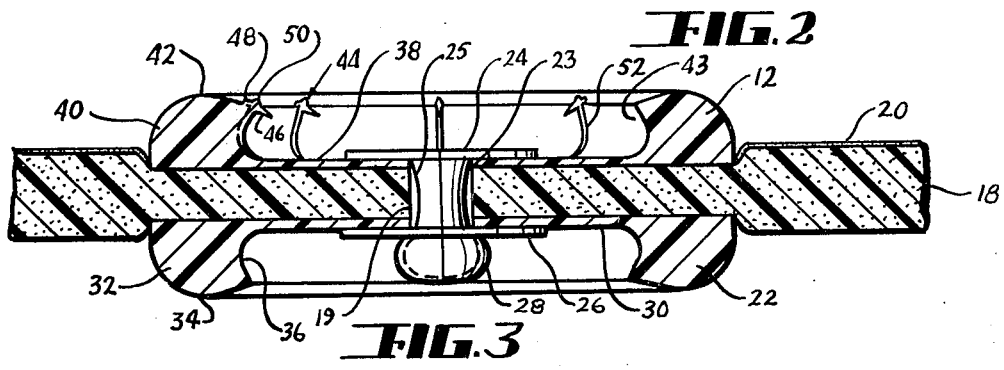
FIG.3

SPONGE RETAINING CUP FOR MEDICAL ELECTRODE

BACKGROUND OF THE INVENTION

This invention relates to cups for medical electrodes of the type in which a sponge or pad loaded with electrolyte is supported within the cup for contact with the skin of a living patient. More particularly the present invention relates to an improved structure for retaining the electrolyte loaded sponge within the cup.

Prior art structures for retaining or otherwise supporting an electrolyte loaded sponge appear in U.S. Pat. Nos. 542,508; 2,651,304; 3,085,577; 3,762,420 and 3,701,346. In U.S. Pat. No. 542,508, an electrolyte pad is retained in a medical electrode by means of a metal plate affixed to the cup body and with the corners of the plate bent over to form posts to engage a sponge. In the second mentioned patent, an electrolyte pad is retained under a re-entrant lip projecting inwardly from a circular cup-like member. Such constructions are found unsuitable for high volume electrode production due to the labor and the general messiness involved in assembly. Thus the electrolyte pad is preferably loaded with a measured quantity of electrolyte gel and such gel is easily squeezed out of the electrolyte pad when the pad is worked under the corners of the plate in U.S. Pat. No. 542,508 or under the re-entrant lip disclosed in U.S. Pat. No. 2,651,304. The result is a lack of control over the signal transmission capabilities of the electrolyte pad.

U.S. Pat. No. 3,805,577 discloses an absorbent electrolyte pad located under a metallic screen and pierced by prongs 23 which are crimped into a snap fastener member. The manufacturing procedures of piercing and crimping preclude the use of a pregelled electrolyte sponge since gel would be pressed out of the pad.

U.S. Pat. No. 3,762,420 illustrates a metal plate supporting the electrolyte sponge or pad having tabs struck therefrom and bent inwardly upon the margin of the electrolyte pad so as to retain the pad. This manufacturing operation again precludes prefilling of the electrolyte pad with a measured quantity of gel which will not be lost by transfer to other surfaces during the manufacture thereof.

U.S. Pat. No. 3,701,346 solves many of the problems of the foregoing prior art structures by providing a cup which loosely receives a prefilled electrolyte sponge or pad and providing a protective cover which overlays the cup and which has a projection therefrom which biases the prefilled sponge or pad into the cup with a minimum of transfer of electrolyte to the protective cover. A difficulty encountered with such construction is that the prefilled sponge or pad is not positively retained in the electrode cup and, particularly when the use of the electrode has been completed, the prefilled sponge sometimes tends to cling to the skin of the patient and thus falls out of the cup when the electrode is being removed from the patient.

SUMMARY OF THE INVENTION

As above indicated it is desirable that the electrolyte sponge or pad of a medical electrode be prefilled with a measured amount of electrolyte so as to assure uniform electrical characteristics when the electrode is placed into use. Such uniform characteristics are desired when the electrode is to be utilized for the purposes of picking up electrical impulses from the skin and also when the electrode is to be used for the purposes of applying electrical impulses to the skin. The foregoing description of the prior art indicates, however, that disadvantages are encountered in the handling of prefilled electrode sponges. An object of the present invention is to provide an electrode cup which can receive and retain a prefilled electrolyte sponge or pad with a minimum of physical handling. It is a further object of the present invention to provide a one-piece electrode cup equipped with suitably located barbs or retention means for retaining the electrolyte sponge against separation from the cup.

The present invention utilizes an injection molded electrode cup having integrally formed barbs extending from the lip of the electrode cup toward the interior of the cup. More particularly the barbs are directed downwardly toward the center of the cup so as to allow a prefilled electrolyte sponge to be dropped or otherwise lowered into the cup without encountering resistance from the barbs. Nevertheless, such barbs because projecting downwardly toward the center of the cup quickly ensnare the prefilled sponge material at any time the sponge material seeks to leave the cup.

BRIEF DESCRIPTION OF THE DRAWINGS

In the drawings,

FIG. 1 is an exploded perspective view of an electrode embodying the present invention.

FIG. 2 is a fragmentary plan view of the electrode before a prefilled electrolyte sponge has been deposited in the cup thereof.

FIG. 3 is a fragmentary section view taken substantially along the line 3—3 of FIG. 2.

FIG. 4 is an enlarged fragmentary section view of the electrode after a prefilled electrolyte sponge has been deposited therein.

DESCRIPTION OF THE PREFERRED EMBODIMENT

FIG. 1 is a perspective view which has been so explode as to indicate the final stages in the manufacture of the electrode. The electrode can be seen to comprise a skin contacting assembly 10, including a cup member 12, which is adapted to receive an electrolyte loaded sponge 14. The electrolyte loaded sponge 14 is ordinarily moist and somewhat sticky. Accordingly, a protective cover 16 is positioned over the sponge 14, as well as the assembly 10, so as to minimize any accumulation of dust and any evaporation of moisture prior to the time that the electrode is placed into use.

Referring to FIG. 3, the assembly 10 comprises a sheet or disc 18 formed of a foamed thermoplastic material such as polyvinylchloride and having one surface thereof coated with a thin layer of a pressure sensitive adhesive 20. As appears in FIG. 1 the disc 18 has a circular outer margin and, as appears in FIG. 3, has a central perforation 19.

The aforementioned cup member 12 has a centrally located perforation 23 passing through the base thereof and is mounted on the adhesive coated side of the sheet 18 with its perforation 23 aligned with the perforation 19 through the sheet 18. A second cup member 22, which is similar to the aforementioned cup member 12 except as will be hereinafter described, is contacted to the opposite side of the sheet 18 in concentric alignment with the cup member 12.

The two cup members 12 and 22 are firmly secured to the sheet 18 by means of a conventional snap fastener assembly comprising a male snap fastener part 24 being a circular plate from which projects a centrally located stud 25, and a female snap fastener part 26 being a circular plate from which has been struck a centrally located socket 28. In assembly of the snap fastener parts, the stud 25 is forced into the socket 28 with a force sufficient to cause the stud 25 to bulge outwardly within the socket 28 and thus form an interlock between the interfitting snap fastener parts. The length of the stud 25 is so sized that the cup members 12 and 22 are caused to compress the foam plastic sheet 18 as the snap fastener parts are driven into interlocking relationship. This compression of the sheet 18 caused the margin of the sheet 18 surrounding the perforation 19 to bulge in the direction of the stud 25.

Referring more particularly to the construction of the cup member 22, it can be seen that the cup member comprises a relatively thin base 30 surrounded by a generally toroidal wall 32 having a smoothly rounded rim 34. The interior surface of the toroidal wall 32 curves radially outwardly so as to undercut a portion of the rim 34 and then merges with the inside surface of the base 30.

The cup member 12 is similarly formed with a base 38 and a toroidal wall 40 having a smoothly rounded rim 42 which is partly undercut by an interior wall 43 which becomes the interior surface of the base 38.

The cup member 12 differs from the cup member 22 by reason of the presence in the cup member 12 of eight equiangularly spaced retaining members 44 extending circumferentially about the interior wall 43. Each of the retaining members 44 can be seen to comprise a barb 46 projecting from the junction between the rim 42 and the interior wall 43 toward approximately the center of the base 38. Forming a foot portion 50 for each of the barbs 46 is a noticeably thickened mass of plastic which diminishes in thickness to form a pad 48 projecting outwardly from the otherwise smoothly rounded rim 42.

Extending downwardly from each of the foot portions 50 to merge with the base 38 is a rib 52 which projects radially inwardly from the interior wall 43, the ribs 52 diminishing in radial inward thickness until they merge with the base 38.

The advantages of the described construction become apparent upon an examination of FIG. 4, which is an enlarged fragmentary illustration of the cup member 12 after an electrolyte soaked sponge has been dropped into the cup member and after the protective cover 16 has been mounted in position. In FIG. 4 it can be seen that the barbs 46 have permitted the gel soaked sponge 14 to slide downwardly into the cup member 12. Importantly, however, the barbs 46 remain poised to seize upon the material of the sponge the instant an upward force would be exerted upon the sponge 14. Thus the sponge drops freely into the position shown in FIG. 4, but is securely retained against withdrawal from the cup member 12 by the barbs 46.

To illustrate the extent of the enlargement embodied in FIG. 4, the cup member 12 may be formed with an outer diameter of approximately 0.955 inch and an opening size, defined by the junction between the rim 42 and the interior wall 43, measuring approximately 0.625 inch in diameter. The radial projection of the barbs 46 from the same junction may then measure approximately 0.022 inch. Considering that the opening size for the cup member may exceed 62 hundredths of an inch and the inward projection of the barbs toward the center of the cup member may be only larger than 2 hundredths of an inch, it can be understood that the barbs 46 are so small in relation to the overall cup member diameter as to freely permit gel soaked sponges to drop into the cup member.

The protective cover 16 is of conventional construction comprising a release paper 54 supporting a hat-shaped cup member 56 having a brim 58. The brim 58 is adhered to the release paper 54 by a suitable adhesive 60. The center of the release paper 54 is cut away to allow the cup member 56 to be seated upon the cup member 12 as shown in FIG. 4. To this end, the interior diameter of the cup member 56 is sized to snugly grip the outer wall of the cup member 12 with the result that the cup member 56 protects the sponge 14 against an excessive evaporation of moisture therefrom and against the entry of dust thereto.

As the protective cover 16 is positioned to cover the cup member 12, the release paper 54 contacts the adhesive 20 with the result that the protective cover is retained in position until the release paper is peeled away from the adhesive 20. When this is done, the cup member 56 separates from the cup member 12 due to the adhesive tack between the release paper 54 and cup member 56.

The preferred thermoplastic for use in fabricating the cup members 12 and 22 is a polyolefin such as high density polyethylene. However, those skilled in the art will recognize that other thermoplastic materials such as polyvinylchloride, polystyrene, and numerous others will function adequately for the cup members 12 and 22.

Although the presently preferred embodiment of this invention has been described, it will be understood that within the purview of this invention various changes may be made within the scope of the appended claims.

Thus having described our invention, we claim:

1. In an electrode cup having a base and a rim defining a cavity for receiving a prefilled electrolyte sponge, said electrode cup having a conductive element attached to said base and communicating with the interior of said cup for transmitting an electrical signal to or from said sponge, barb means affixed to said rim and sufficiently sloping downwardly toward the base of said cup for guiding said sponge when deposited thereon in free sliding movement toward the base of said cup for contact with said conductive element, said barb means poised for snagging said sponge to prevent removal of said sponge from said cup after said sponge has slid on said barb means to the base of said cup.

2. The electrode cup of claim 1 wherein said rim is circular and said barb means includes a plurality of barbs spaced angularly about and projecting from said rim toward the interior of said cup, said barbs projecting downwardly toward the base of said cup.

3. The electrode cup of claim 2 wherein said barbs each project from said rim toward the center of said base, the extent of projection of each of said barbs from said rim being less than about one-twentieth the internal diameter of said rim.

* * * * *